United States Patent [19]

Hogg

[11] Patent Number: 4,932,272

[45] Date of Patent: Jun. 12, 1990

[54] LIQUID SAMPLING VALVE FOR GAS CHROMATOGRAPH

[75] Inventor: Walter T. Hogg, Mississauga, Canada

[73] Assignee: Molson Breweries, Toronto, Canada

[21] Appl. No.: 232,803

[22] Filed: Aug. 15, 1988

[30] Foreign Application Priority Data

Sep. 17, 1987 [CA] Canada .................................. 547148

[51] Int. Cl.⁵ ............................................ G01N 30/20
[52] U.S. Cl. ............................. 73/864.83; 73/863.73; 73/864.84; 73/61.10; 73/23.35
[58] Field of Search ........... 73/863.73, 864.83, 864.84, 73/19, 23.1

[56] References Cited

U.S. PATENT DOCUMENTS

| | | | |
|---|---|---|---|
| 3,746,217 | 7/1973 | Hanset et al. | 73/863.73 X |
| 3,933,165 | 1/1976 | Budzak et al. | 73/863.73 X |
| 3,991,055 | 11/1976 | Godin et al. | 73/864.84 X |
| 4,476,732 | 10/1984 | Yang | 73/863.73 |
| 4,746,491 | 5/1988 | Öhlin | 73/863.73 X |

OTHER PUBLICATIONS

"Sampling Valve for Use in Gas Chromatographic Analysis of the Products of Gaseous Reactions"; *Aids for the Analyst;* vol. 32, No. 9, p. 1213; Aug. 1960; G. L. Pratt et al.

*Primary Examiner*—Tom Noland
*Attorney, Agent, or Firm*—Anthony J. Casella; Gerald E. Hespos

[57] ABSTRACT

A liquid sampling valve for a gas chromatographic analyzer (GCA) has a sampling stem. The stem is substantially cylindrical and has on its surface a sample collecting groove. The stem is movable from a first position in which the groove is in communication with the liquid to be analyzed for collection of same, to a second position in which the liquid collected in the groove is deposited in the GCA for analysis. The stem is also movable to a third position in which the groove is in communication with a cleaning solution capable of cleaning residues, which are left by said liquid to be analyzed, in the groove.

5 Claims, 3 Drawing Sheets

LIQUID SAMPLING VALVE FOR GAS CHROMATOGRAPH

BACKGROUND OF THE INVENTION

The present invention relates to the field of brewing.

More particularly, the present invention relates to an improved liquid sampling valve used in the quantitative analysis, by gas chromatography, of alcohol and carbon dioxide in beer. Even more particularly, the present invention relates to an improved liquid sampling valve which may be used in conjunction with the method and apparatus for the quantitative analysis of carbon dioxide in beer described in the applicant's co-pending Canadian patent application No. 537,187 filed July 30, 1987 for an invention entitled GAS CHROMATOGRAPH MODIFICATION.

Currently, to test beer for alcohol (i.e. ethanol) content or any other component than $CO_2$, it must first be de-gassed (i.e. the $CO_2$ must be removed). This is because conventional laboratory techniques including gas chromatographic analyses are based on the exact measurement of a defined sample quantity (volume or weight); partially de-gassed or carbonated beer samples cannot be measured accurately because of the inherent instability of the sample specimen and as a consequence inaccurate analytical results are obtained. The upshot of the foregoing is it is currently impossible to determine alcohol content in beer accurately with an in-line process gas chromatographic analyzer (GCA). Hence, de-gassification of discrete samples is done prior to alcoholic content determination by a GCA.

Unfortunately, however, when beer is de-gassified prior to analysis, it is inevitable that some ethanol is lost. This further complicates the problem of alcohol determination as the discrete sample which has been de-gassed will no longer be representative of the batch from which it originated.

A further problem associated with the use of a process GCA for ethanol determination is that solids (mainly carbohydrates and proteins) from the beer tend to accumulate in the GCA, necessitating its frequent dis-assembly for cleaning.

The applicant's co-pending patent application aforesaid provides an apparatus by which the alcohol concentration and the carbon dioxide concentration in a pressurized beer sample may be gauged without degassing the beer. It provides an apparatus for use in the in-line chromatographic analysis of, for instance, alcohol or carbon dioxide in beer which apparatus is provided with a CIP (cleaning-in-place) for continuous operation. More particularly, that patent application relates broadly to an apparatus to measure the concentration of a constituent of a solution containing dissolved gas including: (a) conduit means connectable to a source of said solution; (b) flow control means on said conduit means, selectively to permit the flow of said solution in said conduit means; (c) pressure regulation means on said conduit means to control the pressure of said solution in said conduit means, and maintain the pressure in said conduit means at a level sufficiently high to prevent gassification of said dissolved gas in said solution, thereby to prevent foaming in said conduit means; (d) a gas chromatographic analyzer (GCA) in communication with said conduit means via a sampling valve, to permit the flow of discrete samples of said solution into said GCA for analysis, the interior of said GCA being maintained at the same pressure as in said conduit means.

The copending application also relates to a method of measuring the concentration of a constituent in a solution containing a dissolved gas, including the steps of: (a) introducing a quantity of said solution into a pressurizable conduit; (b) pressurizing said solution in said conduit, to prevent gassification of the dissolved gas in the solution; (c) providing a gas chromatographic analyzer (GCA) in communication with said conduit via a liquid sampling valve, and maintaining a pressure in said GCA equal to that in said conduit; (d) measuring the desired constituent concentration in said solution with said GCA.

Referring first to FIG. 1, which corresponds to FIG. 1 of the above referenced Canadian application, a sampling system is provided which may be used to analyze the alcohol content of beer directly from the production lines in a brewery. An analyzer 1 is connected to the production line brewery via a process beer supply line 2. The beer in the line 2 is, of course, carbonated and at sub-ambient temperatures—both of which conditions had previously to be altered before analysis, and neither of which is altered utilizing the present invention. The beer flows through an air actuated valve 3 and is drawn into the sampling area with the aid of pump 4.

The beer flows from the pump 4 to a liquid sampling valve 5, where a quantity can be diverted to a gas chromatographic analyzer 1, which is any suitable standard process GCA unit. Between the line 2 and the analyzer 1, a pressure of 80 psia is maintained in the analyzer by a pressure regulator 6 on the main sample line. Pressure is monitored with a pressure indicator 7 on this line. The pressure in the sample line is necessary to deliver a uniformly liquid sample to the analyzer. Maintenance of this pressure prevents the undesired separation of carbon dioxide from the liquid which otherwise would result in foam in the sample line. The size of the injected beer sample is predetermined and relatively small (0.5 microliter) and foam in the sample line would lead to inaccurate measurements.

The major part of the beer flowing through the sampling line will not be diverted to the analyzer, but will re returned via return line 8 and will pass through air actuated drain/process return valve 10 to process return line 9, which flows to the main production line in the brewery.

It has been found, using the system outlined above, that by maintaining back pressure in the sampling line and similar pressure in the GCA, a sample with a $CO_2$ content can be analyzed, with no fluctuation upon vaporization in the GCA to cause unreproducable results.

To calibrate the GCA 1 calibration standard (having a known concentration of the thing to be analyzed) is taken in through line 11, past flow indicator 12 and through air actuated valves 13 and 3 to the sampling area described above, where a sample of the known standard is analyzed to calibrate the analyzer 1. Of course, a series of known standards must be analyzed before calibration of the analyzer is complete. Also, it will be noted that valve 10 will be open to drain line, rather than process return line 9 during calibration.

The system of FIG. 1 also has a clean-in-place (CIP) sub-system built into it. Lines 15 and 16 respectively feed hot water and cleaning solvent into the CIP sub-system, from whence it can be allowed to flow into the main sampling system. A pressure regulator 17 and pressure indicator 18 are provided on the hot water line, to ensure that the pressure in this line is kept at acceptable levels (as will be a matter of choice to one skilled in the brewing art and especially in plant maintenance). Also, a flow indicator is provided on the hot water line so that a suitable quantity of hot water may easily be mixed with the solvent solution in-put through line 16.

Carefully measured quantities of cleaning solution are drawn through line 16 by metering pump 20 and pass through pressure indicator 21, flow indicator 22 and valve (air actuated) 23 to mixing coil 24. At the same time as when cleaning solution is let into coil 24, air actuated valve 25 on the hot water line is opened to allow hot water into the coil 24 and after the water and solution are mixed, air actuated valve 26 is opened and valves 13 and 3 are opened to permit a flow of mixed water and cleaning solution to pass through the sampling area and clean any deposited solids therefrom.

Valve 10 should, of course, be set to drain line 14 to permit used solution to be disposed of. After the sampling system has been cleaned with cleaning solution, it is flushed with hot water by opening valve 25 to by-pass line 27 (to by-pass coils 24), closing valve 23 and opening valves 26, 13, 3 and 10 to permit hot water flow through the sampling area and out the drain.

The system of pressurized gas chromatography of the above referenced copending application may also be used in laboratory analysis of discrete samples (bottles or cans) of finished product beer, for quality control as illustrated schematically in FIG. 2.

A container 27, either a bottle or can of beer is placed in holder 28 which holds it securely while a sampling mechanism 29 is pneumatically driven into the container 27 to draw out the contents thereof. These contents flow through sampling line 30 through sampling valve 31 into the sampling loop 32 and through sampling pump 33 used to develop 80 PSI in the sampling loop 32. The loop further includes a pressure regulator 34 and pressure indicator 35, for accurate regulation and monitoring of the pressure in the loop 32.

A liquid sampling valve 36 on the loop 32 is used to divert samples to GCA 37, the column of which is kept pressurized at 80 PSI.

Completing the sampling loop is loop drain valve 38 which may be opened to drain line 39 when analysis is complete or to loop return line 40 for the actual sampling procedure. When fluid is injected into the loop from sampling mechanism 29, it fills the loop, at which time valve 38 is closed to drain line 39 and opened to loop return line 40. Simultaneously, valve 31 is closed, which completes the loop, and permits pressurization thereof. To analyze the next sample, valve 38 is opened to drain line 39 and the sample in the loop discharged; the cycle is then repeated.

The laboratory system illustrated in FIG. 2 also includes a cleaning sub-system, much modified from the fill in-line CIP system disclosed above. The cleaning sub-system of the FIG. 2 apparatus is merely a line 41 provided with a valve 42 and a flow indicator 43, into which line, and thence into the loop, may be injected cleaning solution, hot rinse water or calibration standard solution.

Since the reason for the provision of a cleaning-in-place system which washes out the entire conduit system provided in the applicant's aforesaid patent application, it is the object of the present invention to provide a modified sampling valve and a modified cleaning-in-place sub-system which overcomes the drawback identified above, and thereby decreases down-time and complexity associated with using the invention described in the applicant's aforesaid co-pending patent application.

SUMMARY OF THE INVENTION

In one broad aspect, the present invention relates to a liquid sampling valve for a gas chromatographic analyzer (GCA), said valve having a sampling stem, said stem being substantially cylindrical and having on its surface a sample collecting groove, said stem being movable from a first position in which said groove is in communication with the liquid to be analyzed for collection of same, to a second position in which said liquid collected in said groove is deposited in said GCA for analysis, characterized in that said stem is also movable to a third position in which said groove is in communication with a cleaning solution capable of cleaning residues which are left by said liquid to be analyzed in said groove.

BRIEF DESCRIPTION OF THE DRAWINGS

In drawings which illustrate the present invention by way of example.

DETAILED DESCRIPTION OF THE PREFERRED EMBODIMENT

Figure 1:
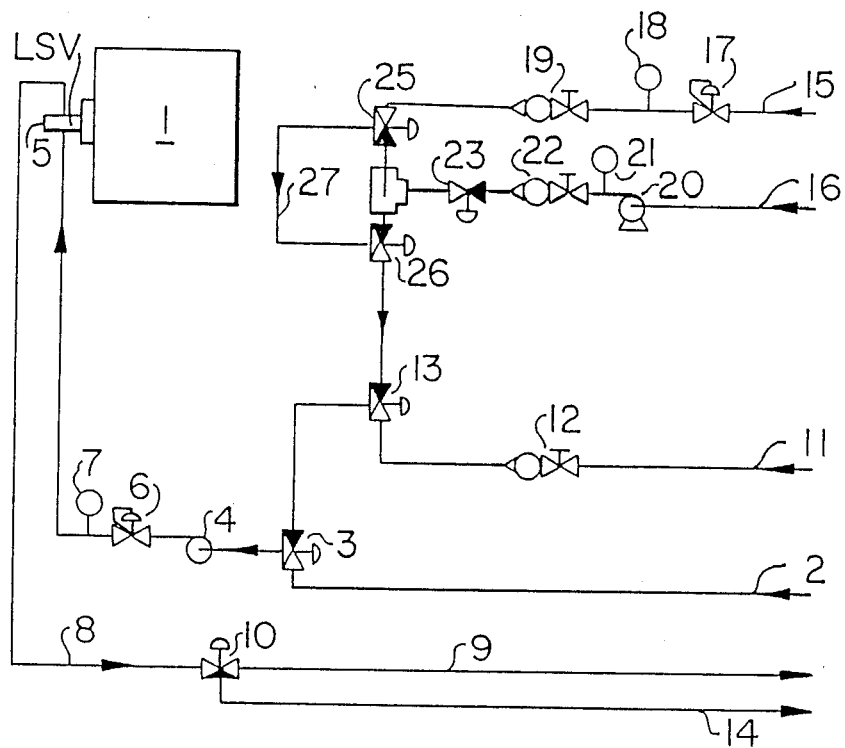
FIG. 1 is a schematic of a system for the in-line determination of alcohol content in beer as disclosed in Canadian patent application No. 537,187.
Figure 3:
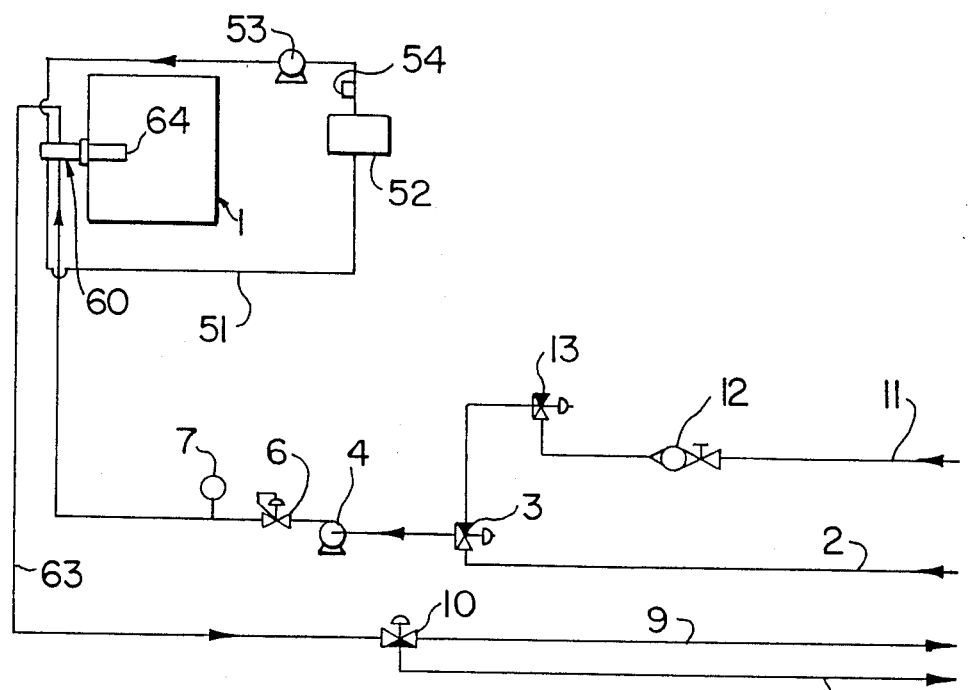
FIG. 3 is a schematic of a system for the in-line determination of alcohol content in beer as disclosed in Canadian patent application No. 537,187, but employing the present invention.

Referring first to FIG. 3, it will be seen that the system shown therein is similar in many respects to the system shown in FIG. 1. The differences are that a different liquid sampling valve 60, which will be described below is provided, and the cleaning-in-place system which was provided in the system shown in FIG. 1 has been eliminated and replaced with a modified and simplified system. In particular, the cleaning-in-place system provides a loop conduit 51 in which cleaning solution may be continually circulated via pump 53 through the conduit 51 which may be provided with a reservoir 52 for collecting cleaning fluid and a filter 54 for filtering out any solids which may collect in the cleaning fluid. The loop conduit 51 is in communication with the modified liquid sampling valve 60 directly, and does not serve to wash out any of the beer lines provided in the overall system, since it has been found that the only solids contamination which is significant is directly in the groove. This is because the small capacity of the groove—from one-half to one microliter typically—tends to magnify the extent of any residue contamination.

Figure 2:
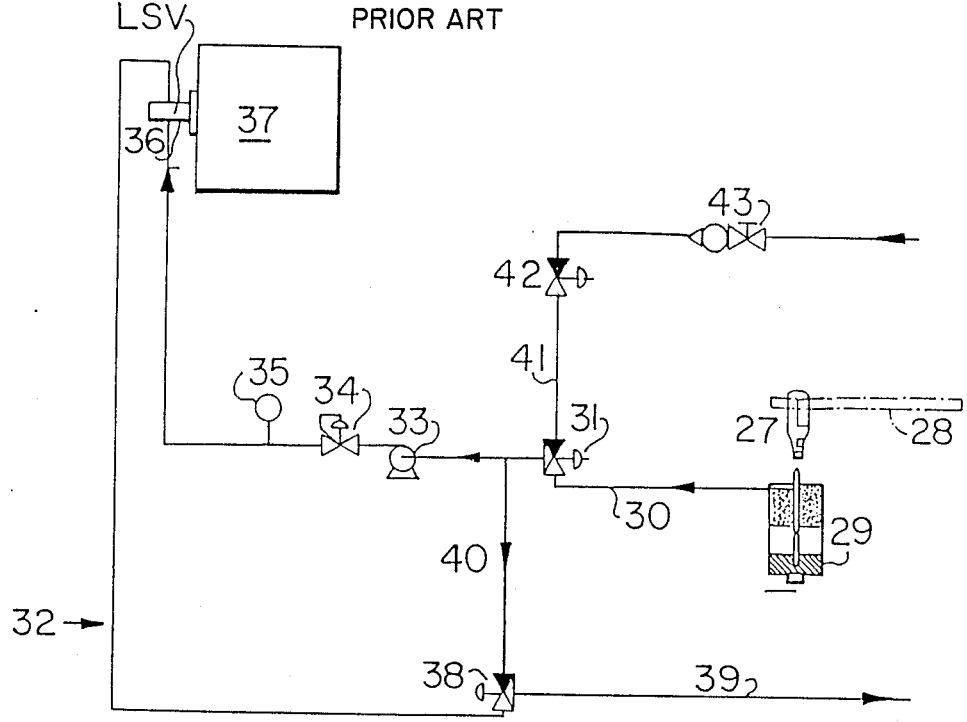
FIG. 2 is a schematic of a system for the laboratory analysis of the alcohol content of discrete samples in beer as described in Canadian patent application No. 537,187.
Figure 4:
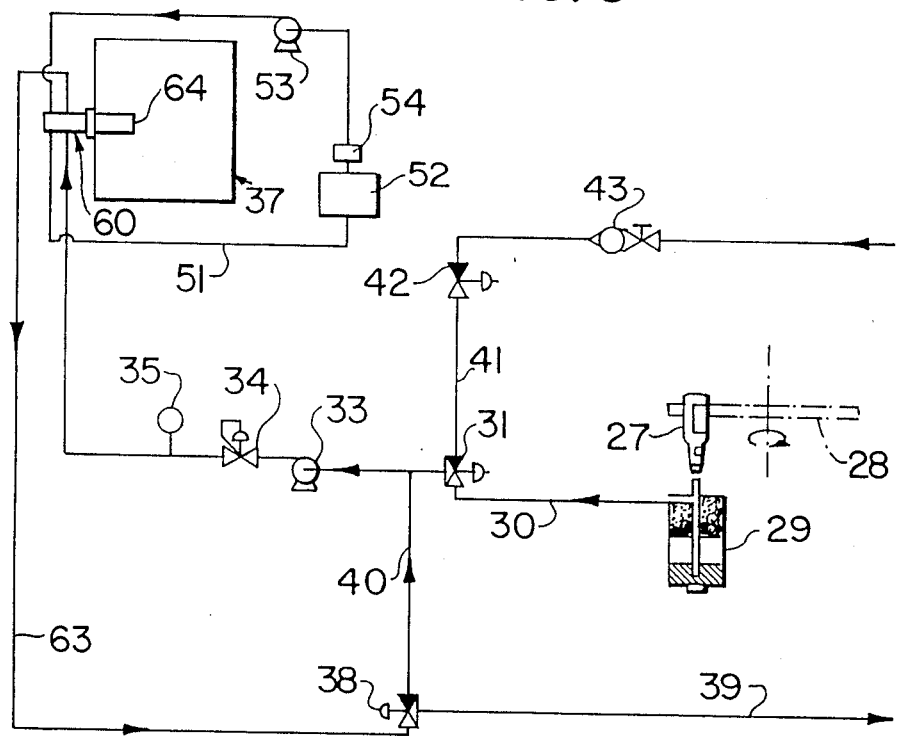
FIG. 4 is a schematic of a system for the laboratory analysis of the alcohol content of discrete samples in beer as described in Canadian patent application No. 537,187, but employing the present invention.

Before moving on to a description of the liquid sampling valve which is provided, it can be seen from FIG. 4 that the laboratory system provided in FIG. 2 is modified by the inclusion of a cleaning-in-place system and a modified liquid sampling valve, as provided in the present invention, all as shown in FIG. 4. In such an embodiment, the cleaning-in-place system provided in the prior art system described in FIG. 2 will be used almost exclusively for calibration standard.

Moreover, it will be noted from both FIGS. 3 and 4 that there is no necessity of having a hot water rinse line in association with the cleaning-in-place loop 51 of the present invention. This is because the only part of the analysis system with which the cleaning solution of the loop will be in contact is the liquid sampling groove and as stated above, a volume of only one-half to one microliter of cleaning solution will be contained in the liquid sampling groove at any one time. Such a small volume will leave negligible residues.

Figure 5:
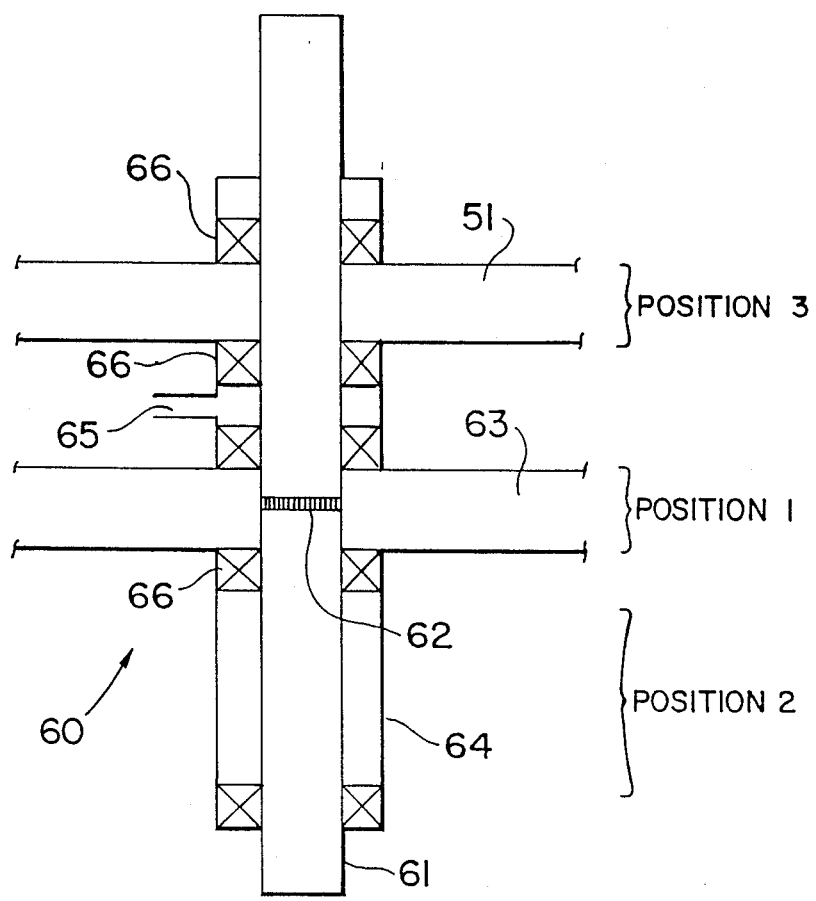
FIG. 5 is a partially schematic cross-sectional diagram of a liquid sampling valve employing the present invention.

Turning now to the structure of the all important liquid sampling valve 60, which makes the continuous loop cleaning-in-place system of the present invention possible, reference may now be made to FIG. 5. It will be seen from FIG. 5 that a stem 61 movable by the actuator of a GCA (not shown) is provided with a sampling groove 62 around its circumference (the stem being cylindrical). This groove is calibrated precisely to hold a predetermined volume of liquid, usually from 0.5 to 1.0 microliters. The stem extends transverse to the beer flow line 63 and above it also transverse to the cleaning solution loop conduit 51. The stem extends through bores in each of these lines, there being pressure and liquid tight seals 66 around the stem at the points of intersection with the lines. It will be noted that between the solution line and the beer line the stem is open to the atmosphere, to permit any solution which may have accumulated in the groove 62 to drip out, which will also prevent any cross-contamination which may result by a mixing of the beer stream and the cleaning stream. Alternatively, a third line of constantly circulating water may be provided between the beer and the solution lines (this third line not being shown) to rinse the sampling groove between the solution line and the beer line.

In operation, the stem 61 of the liquid sampling valve begins in a resting position wherein the sampling groove is in cleaning solution line 5. When it is desired to take a sample of the beer in line 63, the stem is moved downwardly so that the groove goes through the vented area 65 (which may be provided with a water line as noted above) and then through the beer line 63 and down in the oven 64 of the GCA. All of the beer which has accumulated in the groove will be evaporated in the oven for analysis. The groove will have a residence time in the oven of about 15 seconds. The stem is then moved upwardly into the beer line and reciprocally between the beer line and the oven as samples are desired, until about fifty samples have been taken, at which point the groove ought to be cleaned and the stem is therefore moved up so that the groove is once again in the solution line, where is it permitted to remain for about three minutes, or until such shorter or longer time as it takes for cleaning. It will be seen that in this way, the down time of the system is extremely low.

It is to be understood that the examples described above are not meant to limit the scope of the present invention. It is expected that numerous variants will be obvious to the person skilled in the brewing or quantitative analysis arts, without any departure from the spirit of the present invention.

I claim:

1. A liquid sampling valve for a gas chromatographic analyzer (GCA), said valve having a sampling stem, said stem being substantially cylindrical and having on its surface a sample collecting groove, said stem being movable from a first position in which said groove is in communication with the liquid to be analyzed for collection of same, to a second position in which said liquid collected in said groove is deposited in said GCA for analysis, characterized in that said stem is also movable to a third position in which said groove is in communication with a cleaning solution capable of cleaning residues which are left by said liquid to be analyzed in said groove, said first position being between said second and third positions, said stem being movable from said first to said second position repeatedly without said groove being in communication with said cleaning solution, and a cleaning-in-place (CIP) sub-system for an apparatus for the quantitative analysis of constituents of a liquid by gas chromatography, said CIP including a pipeline for piping cleaning fluid around a closed loop, said loop being in communication with said liquid sampling valve, the interior of the piping thereby defining said third position.

2. A liquid sampling valve as described in claim 1 further characterized in that a space is provided between said first and said third positions whereby said groove is vented when moving from said third to said first positions.

3. A liquid sampling valve as described in claim 1, further characterized in that a source of rinse water is provided between said first and third positions, thereby said groove is rinsed when moving from said third to said first position.

4. The combination of claim 1, wherein the said groove is circumferential, and said stem intersects said piping through a bore transverse to a longitudinal axis of the piping, there being seals provided between said stem and said piping.

5. The combination of claim 4, wherein said CIP sub-system includes a pump for propelling cleaning solution around said closed loop of piping, a reservoir for collecting cleaning fluid, situated on said loop as an integral part thereof, and a filter situated on said loop as an integral part thereof.

* * * * *